(12) United States Patent
Hempel

(10) Patent No.: US 7,532,704 B2
(45) Date of Patent: May 12, 2009

(54) X-RAY CT SYSTEM FOR PRODUCING PROJECTIVE AND TOMOGRAPHIC PHASE CONTRAST IMAGES

(75) Inventor: Eckhard Hempel, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 143 days.

(21) Appl. No.: 11/700,153

(22) Filed: Jan. 31, 2007

(65) Prior Publication Data

US 2007/0183559 A1     Aug. 9, 2007

(30) Foreign Application Priority Data

| Feb. 1, 2006 | (DE) | 10 2006 004 604 |
| Feb. 1, 2006 | (DE) | 10 2006 004 976 |
| Sep. 28, 2006 | (DE) | 10 2006 046 034 |

(51) Int. Cl.
    *A61B 6/00* (2006.01)
(52) U.S. Cl. ......................................... 378/19; 378/145
(58) Field of Classification Search ............... 378/4–20, 378/145, 147, 149, 154, 155
    See application file for complete search history.

(56) References Cited

U.S. PATENT DOCUMENTS

| 7,046,757 | B1 | 5/2006 | Bani-Hashemi et al. ........ 378/7 |
| 2007/0183560 | A1* | 8/2007 | Popescu et al. ................ 378/5 |

OTHER PUBLICATIONS

A. Momose et al.: "Phase Tomography by X-ray Talbot Interferometer", SRI 2006.
F. Pfeiffer et al.: "Phase retrieval and differential phase-contrast imaging with low-brilliance X-ray sources", Nature Physics 265, 2006, published online Mar. 26, 2006.
T.Weitkamp et al.: "X-ray phase imaging with a grating interferometer", Optics Express, vol. 13, No. 16, published Aug. 8, 2005, pp. 6296-6304.

\* cited by examiner

*Primary Examiner*—Courtney Thomas
(74) *Attorney, Agent, or Firm*—Harness, Dickey & Pierce, P.L.C.

(57) ABSTRACT

An X-ray CT system is disclosed for producing tomographic phase contrast and absorption images. In at least one embodiment, the system includes a gantry, including a stationary stator and a first rotor supported on the stator and rotates relative to the stator about a system axis, at least one X-ray source detector system that can rotate about a patient and a system axis and is arranged on the first rotor, and at least one set of X-ray optical gratings for determining phase contrast. According to at least one embodiment, the at least one set of X-ray optical gratings is arranged such that it can be displaced relative to the first rotor of the gantry.

20 Claims, 5 Drawing Sheets

X-RAY CT SYSTEM FOR PRODUCING PROJECTIVE AND TOMOGRAPHIC PHASE CONTRAST IMAGES

PRIORITY STATEMENT

The present application hereby claims priority under 35 U.S.C. §119 on German patent application numbers DE 10 2006 004 604.8 filed Feb. 1, 2006, DE 10 2006 004 976.4 filed Feb. 1, 2006, and DE 10 2006 046 034.0 filed Sep. 28, 2006, the entire contents of each of which is hereby incorporated herein by reference.

FIELD

Embodiments of the invention generally relate to an X-ray CT system for producing tomographic phase contrast and absorption images. For example, it may relate to one having a gantry that has a stationary stator and a first rotor, which is supported on the stator and rotates relative to the latter about a system axis, at least one X-ray source detector system that can rotate about a patient and a system axis and is arranged on the first rotor, and at least one set of X-ray optical gratings for determining phase contrast.

BACKGROUND

In general computed tomography, tomographic images of an examination object, in particular of a patient, are taken with the aid of absorption measurements of X-rays that penetrate the examination object, a radiation source generally being moved in the shape of a circle or spiral about the examination object, and for the most part, a multirow detector with a multiplicity of detector elements, measuring the absorption of the radiation upon passage through the examination object on the side of a detector opposite the radiation source. For the purpose of tomographic imaging, tomographic slice images or volume data are reconstructed from the measured absorption data of all the measured spatial rays. Very fine absorption differences in objects can be displayed with the aid of these computed tomography images, but zones of similar chemical composition that naturally also have a similar absorption behavior are displayed only with unsatisfactory detail.

It is known, furthermore, that the effect of the phase shift upon passage of a beam through an examination object is substantially stronger than the absorption effect of the material penetrated by the radiation. Such phase shifts are known to be measured by the use of two interferometric gratings. These interferometric measuring methods are referred to, for example, in "X-ray phase imaging with a grating interferometer, T. Weitkamp et al., Aug. 8, 2005/Vol. 12, No. 16/OPTICS EXPRESS".

In the case of this method, an examination object is irradiated by a coherent X-radiation and subsequently guided through a pair of gratings, and the radiant intensity is measured directly after the second grating. The first grating produces an interference pattern that images a moiré pattern on to the detector lying therebehind with the aid of the second grating. If the second grating is slightly displaced, this likewise results in a displacement of the moiré pattern, that is to say a change in the spatial intensity in the detector lying therebehind, which can be determined relative to the displacement of the second grating. If the change in intensity is plotted for each detector element of this grating that is to say for each beam, as a function of the displacement path of the second grating, the phase shift of the respective beam can be determined. The fact that this method requires a very small radiation source is a problem, and therefore cannot be applied in practicing computed tomography of relatively large objects, since formation of the interference pattern requires a coherent radiation.

In one possibility, the method shown in the abovenamed document requires a radiation source with an extremely small focus such that a sufficient degree of spatial coherence is present in the radiation used. However, when such a small focus is used there is then, in turn, an insufficient dose rate for examining a relatively large object. However, there is also the possibility of using a monochromatically coherent radiation, for example, a synchrotron radiation, as radiation source, but the construction of the CT system is thereby rendered very expensive and so a widespread application is impossible.

This problem can be circumvented by arranging a first absorption grating inside the focus/detector combination in the beam path, directly following the focus. The alignment of the grating lines is in this case parallel to the grating lines of the interference grating following the examination object.

The slits of the first grating produce a field of individually coherent beams that suffices for producing the interference pattern known per se with the aid of the phase grating arranged downstream of the object in the beam direction. It is possible in this way to use radiation sources that have dimensions corresponding to the normal X-ray tubes in CT systems or transmitted light X-ray systems such that, for example, it is now also possible to make well differentiated soft part images in the field of general medical diagnostics with the aid of X-ray machines. Reference is made in this regard to the German patent applications, which are not prior publications, having the file numbers 10 2006 017 290.6, 10 2006 015 358.8, 10 2006 017 291.4, 10 2006 015 356.1 and 10 2006 015 355.3, the entire disclosure content of each of which is hereby incorporated herein by reference.

The use of such X-ray optical gratings in conjunction with X-ray CT systems is, however, very demanding technically since these X-ray optical gratings require structures with a very high contrast ratio, for example 100 µm, and at the same time require a very short period of the order of magnitude of 2 µm, corresponding to web widths of approximately 1 µm. Moreover, the aim is to use strongly absorbing material for these gratings, ideally to use gold. At the same time, it is described in the abovenamed documents that the data obtained from the phase contrast measurement are also available for the absorption tomographic imaging. However, the problem thereby arises that this leads to a strong radiation burden on the patient because of the required strong absorption of the X-ray gratings. Consequently, such CT systems with permanently installed X-ray optical gratings in the beam path between the patient and the detector system cannot also be used regularly for absorption CT.

SUMMARY

In at least one embodiment of the invention, a CT system is disclosed that is more flexibly suitable both for producing absorption CT images and for producing phase contrast CT images, the imaging being achieved in each case with the smallest possible dose commitment for the patient.

The inventor correspondingly proposes, in at least one embodiment, the improvement of an X-ray CT system for producing tomographic phase contrast and absorption images, comprising a gantry that has a stationary stator and a first rotor, which is supported on the stator and rotates relative to the latter about a system axis, at least one X-ray source detector system that can rotate about a patient and a system axis and is arranged on the first rotor, and at least one set of X-ray optical gratings for determining phase contrast. The improvement resulting from the fact that the at least one set of X-ray optical gratings is arranged such that it can be displaced relative to the first rotor of the gantry. It is thereby rendered possible to prepare tomographic absorption images given a continuously low radiation burden and to use the same apparatus to produce phase contrast images, the higher radiation burden required therefor needing to be accepted.

This X-ray CT system can advantageously be designed such that the at least one set of X-ray optical gratings covers only a part of the detector in the operating state. For the most part, the part of the patient considered by the phase contrast examination is substantially smaller in cross section than the overall cross section of the patient and so the radiation of the irrelevant body parts can be reduced during the examination.

According to at least one embodiment of the invention, in addition to the rotor on which the X-ray source and the detector are fastened, the gantry can have a displacing apparatus on which the X-ray optical gratings which can be arranged on the beam path are fastened, and with the aid of which said gratings can be displaced from the and into the beam path of the X-ray source. In this case, the displacing apparatus on which the X-ray optical gratings, which can be arranged in the beam path are fastened, is designed in the shape of a circular segment or as a complete annular component, in order to displace the gratings in the circumferential direction. Alternatively, it is also possible to arrange on the rotor a telescope-like or rail-like displacing apparatus by means of which the gratings can be displaced in the direction of the system axis.

Furthermore, the X-ray source of the CT system according to at least one embodiment of the invention can have a diaphragm with the aid of which the beam cone emitted by the source can be adapted to the extent of the X-ray optical gratings or of the overall detector.

Moreover, it is particularly advantageous when, in at least one embodiment, the X-ray source has a source grating by which quasi-coherent X-radiation can be generated at a high dose rate, it being possible as a result to keep the duration of the examination as short as possible.

In accordance with a further aspect of at least one embodiment of the invention, the inventor also proposes an X-ray CT system for producing tomographic phase contrast and absorption images that has a gantry with a stationary stator and a first rotor, which is supported on the stator and rotates relative to the latter about a system axis, and at least one X-ray source detector system that can rotate about a patient and a system axis and is arranged on the first rotor, in which at least one set of X-ray optical gratings determining phase contrast are located. In this case, the improvement resides in the fact that a first beam path is provided exclusively for the purpose of absorption measurement and a second beam path, arranged offset in the direction of the system axis, is provided for the purpose of phase contrast measurement.

In the case of such an X-ray CT system, the gantry can have a second rotor, one detector being arranged on the first rotor for the purpose of absorption measurement, and a second detector being arranged on the second rotor exclusively for the purpose of phase contrast measurement with the aid of the set of X-ray optical gratings. It is also advantageous for a dedicated X-ray source to be arranged on each rotor.

BRIEF DESCRIPTION OF THE DRAWINGS

The invention is described in more detail below with reference to an example embodiment and with the aid of the figures, only the features necessary for understanding the invention being illustrated. The following reference symbols are used in this case: 1: X-ray CT system; 2, 2': X-ray tube; 2.1: focus; 2.2: source grating; 2.3: movable diaphragms; 3, 3': detector system; 4: phase grating; 4': swung-out phase grating; 5: analyzer grating; 5': swung-out analyzer grating; 6: gantry housing; 7: patient; 8: movable patient table; 9: system axis; 10: arithmetic logic unit; 11: memory of the arithmetic logic unit; 12, 12': rotor; 13: stator; 14: displacing apparatus of the type of a circular segment for the set of X-ray optical gratings; 15: conical measuring field for the absorption measurement; 16: conical measuring field for phase contrast measurement; 17.1, 17.2: telescopic rails in the direction of the system axis for moving the set of X-ray optical gratings in and out; $Prg_1$-$Prg_n$: computer programs.

In detail.

DETAILED DESCRIPTION OF THE EXAMPLE EMBODIMENTS

Figure 1:
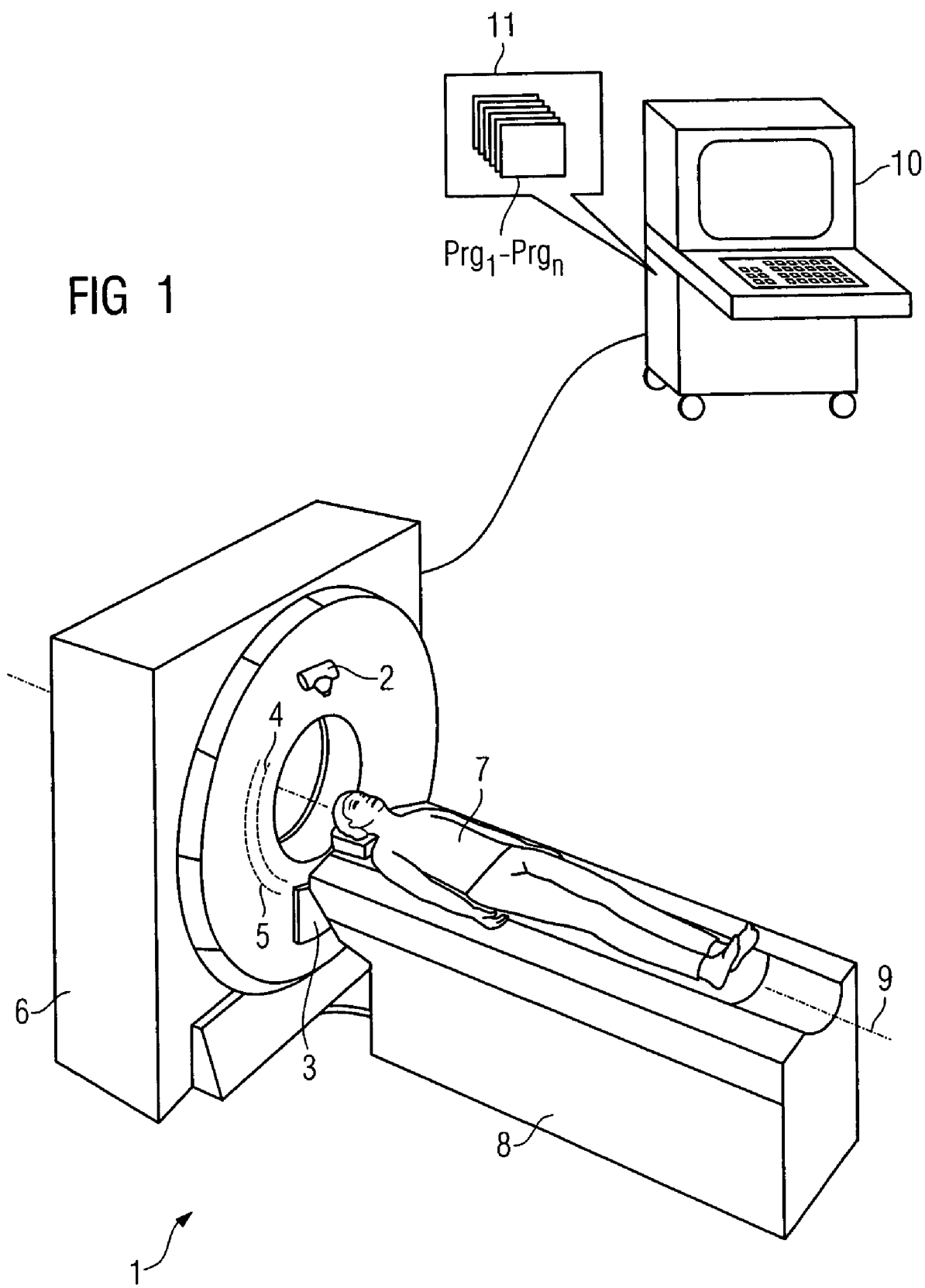
FIG. 1: shows a 3D schematic of an X-ray CT system according to an embodiment of the invention.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows a 3D schematic of an X-ray CT system 1 according to an embodiment of the invention, having a gantry housing 6 in which an X-ray tube 2 with a detector 3 situated opposite is located as X-ray source. In addition, a phase grating 4 and an analyzer grating 5 are provided for measuring phase contrast. The phase contrast grating 4 and the analyzer grating 5 are arranged such that they can be swung out of the measuring range of the detector 3 in the circumferential direction of the gantry—which is not illustrated specifically here.

For the purpose of measurement, a patient 7 who is located on a movable patient couch 8 is pushed along the system axis 9 into an opening in the measuring range of the detector system, the X-ray tube with the detector situated opposite and the set of X-ray optical gratings including the phase grating 4 and the analyzer grating 5 being moved for the purpose of the actual measurement around the patient 7 such that a multiplicity of projective absorption data and projective phase contrast data are measured from different recording angles and are subsequently reconstructed in the arithmetic logic unit 10 with the aid of computer programs $Prg_1$-$Prg_n$ that are included in the memory 11 of the arithmetic logic unit 10.

According to an embodiment of the invention, in order to avoid an excessively high dose rate it is possible with these measurements to move the set of X-ray optical gratings 4 and 5 that absorbs the radiation out of the measuring range of the detector 3 for the purpose of absorption measurement such that the absorption measurement can be carried out with as little radiation burden as possible for the patient 7. At the same time, however, it is possible to move the X-ray optical gratings 4 and 5 into the measuring range of the detector 3 for the purpose of phase contrast measurement, and then to carry out a phase contrast measurement in a way known per se.

Figure 2:
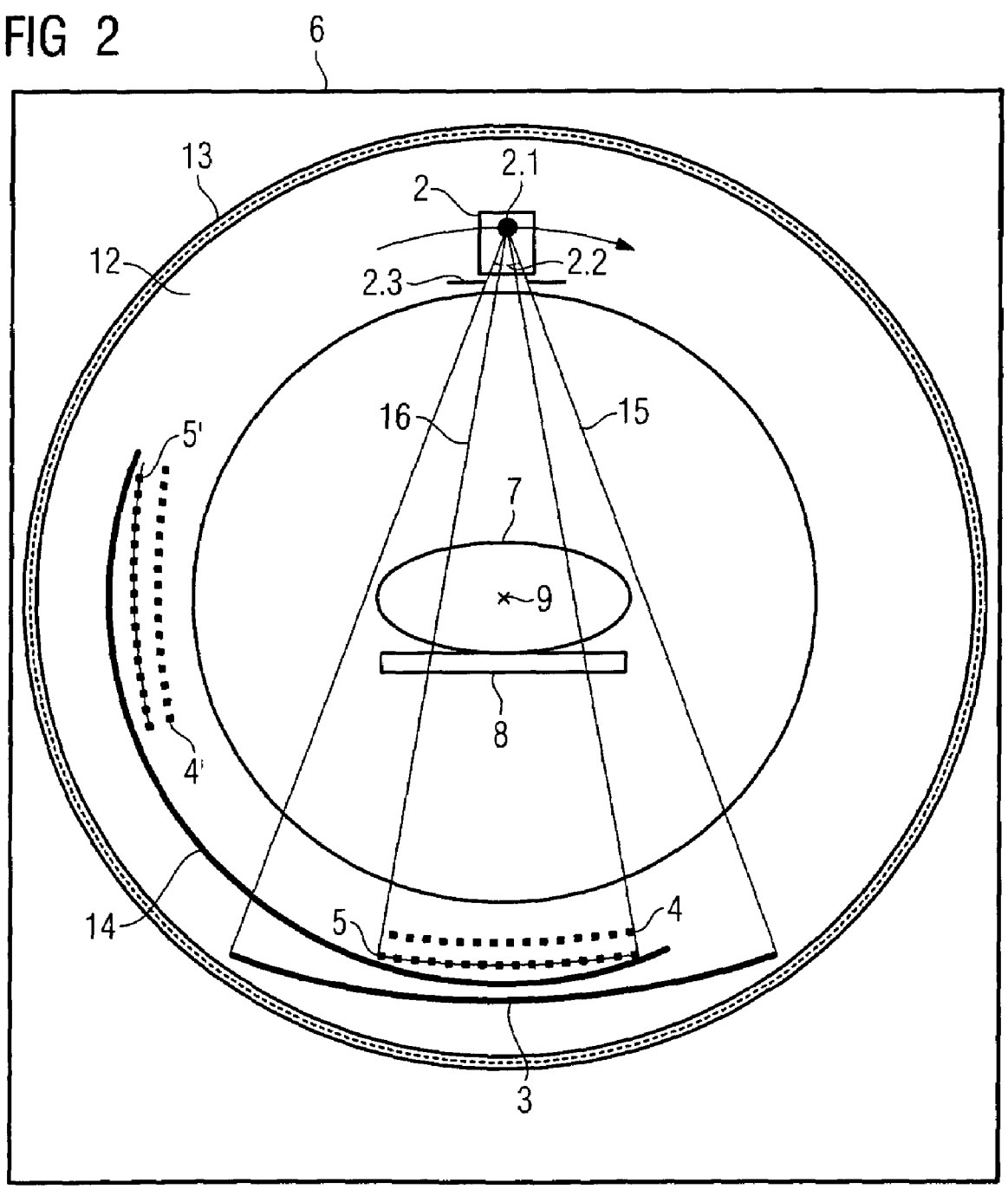
FIG. 2: shows a sectional illustration of an X-ray CT system according to an embodiment of the invention with a set of X-ray optical gratings that can be displaced in the circumferential direction.

FIG. 2 shows the situation once again in cross section. Illustrated here again is the gantry housing 6 in which there is located a stationary stator 13 in the gantry that supports the rotor 12. Fastened on the rotor 12 are both the X-ray tube 2 and the detector 3, situated opposite, which is mostly designed as a multirow detector. Emitted from the focus 2.1 in the X-ray tube is radiation that can be regulated via adjustable diaphragms 2.3 with reference to the cone beam produced, such that either a wide radiation cone 15 that covers the complete detector 3 is exposed, or a narrower radiation cone 16 is set. This narrower radiation cone 16 strikes the X-ray optical gratings 4 and 5, which likewise cover the detector only partially and can be used to measure phase contrast over a subregion of the detector 3. These X-ray optical gratings 4 and 5 can be swung out of the measuring range of the detector 3 in the circumferential direction with the aid of a displacing mechanism 14 of the type of a circular segment such that optionally either exclusively absorption measurement is carried out or phase contrast measurement is executed on a reduced measuring field 16.

Figure 3:
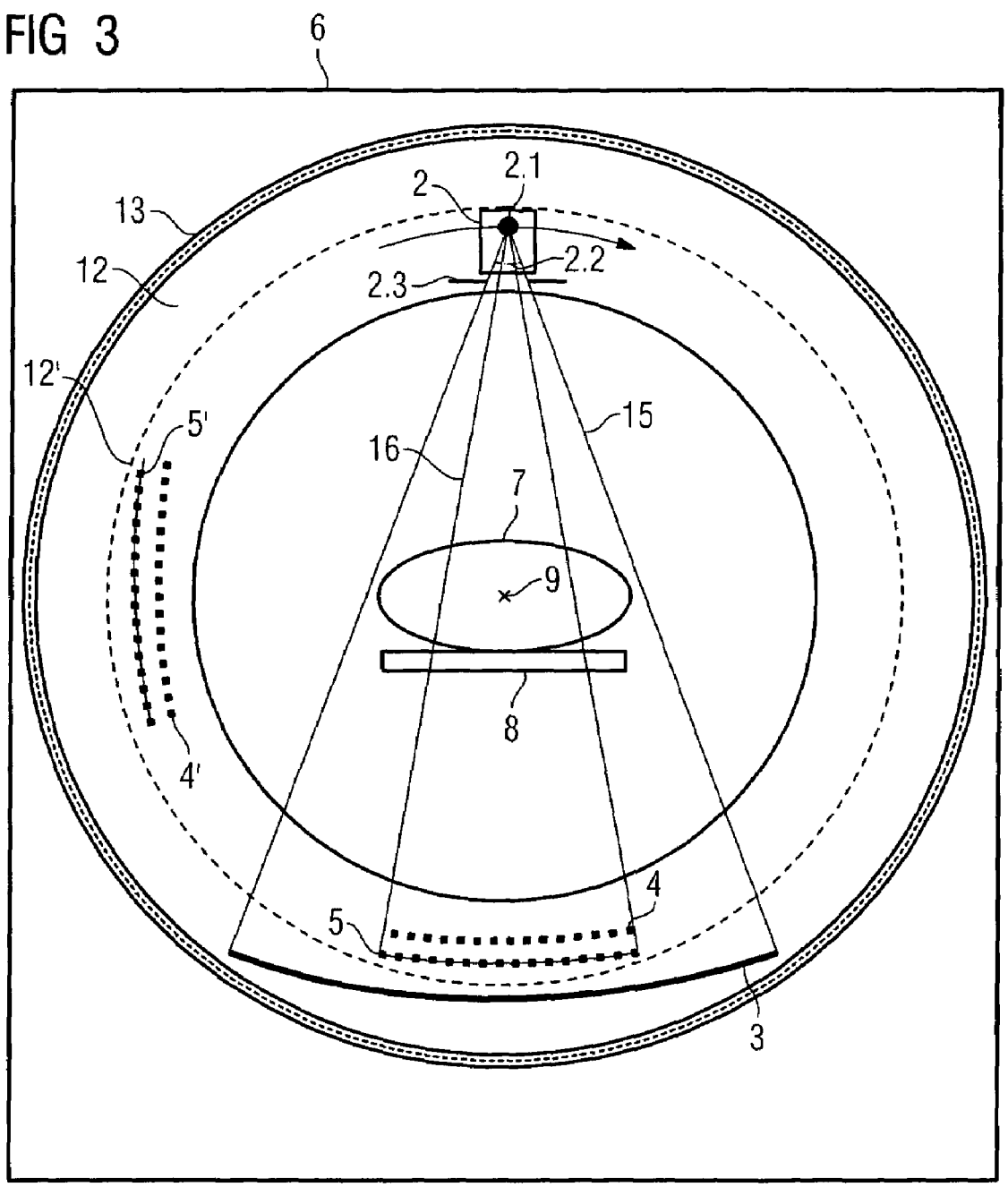
FIG. 3: shows a sectional illustration of an X-ray CT system in accordance with FIG. 2, but with a revolving displacing apparatus for the X-ray optical gratings.

FIG. 3 shows the same CT system as in FIG. 2, but the displacing mechanism 14 of the type of a circular segment in FIG. 2 is designed as a closed ring such that it corresponds to a second rotor 12' in the gantry with the aid of which the gratings 4 and 5 can be displaced circularly around the system axis in a fashion similar to the X-ray tube and the detector.

Figure 4:
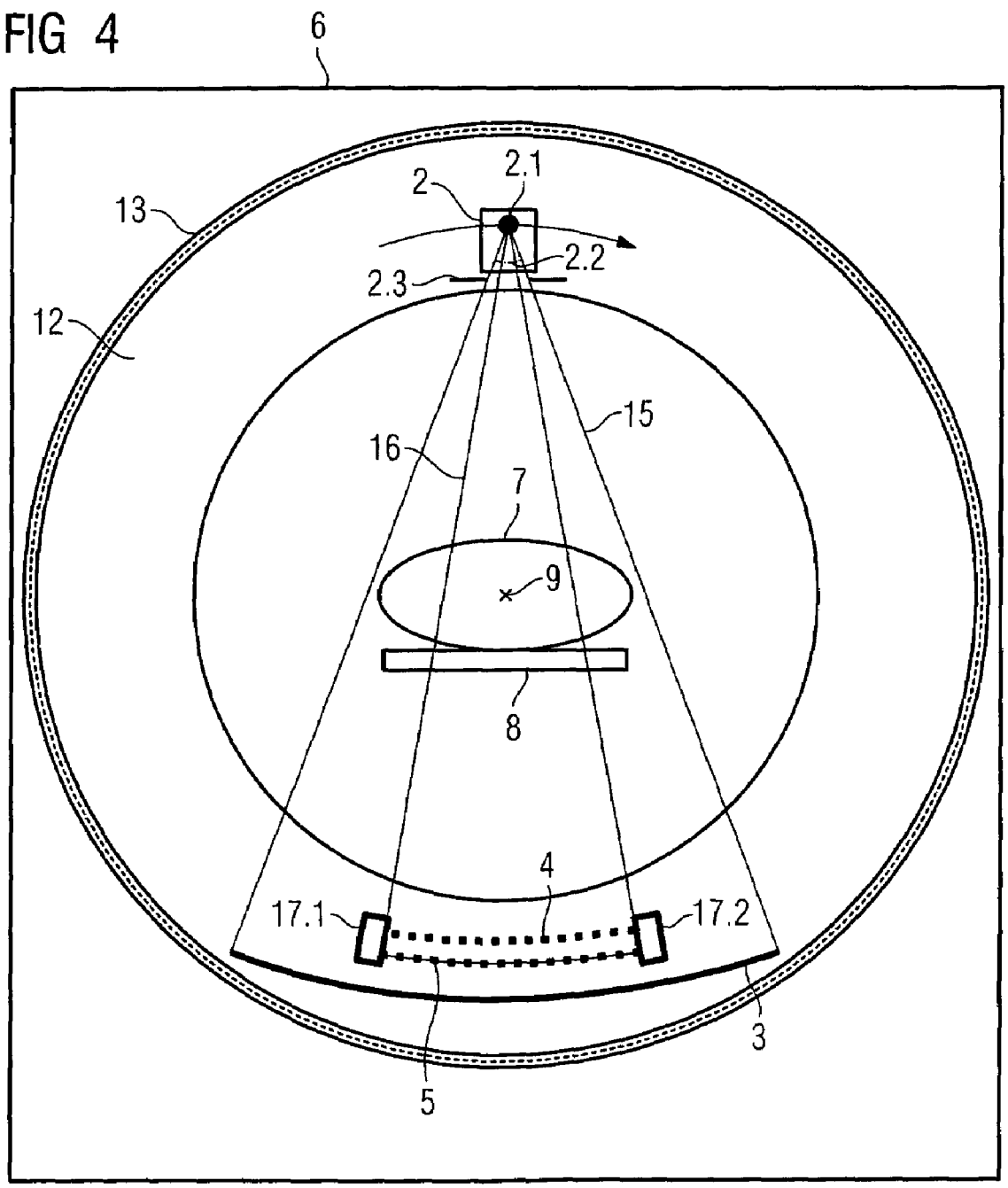
FIG. 4: shows a sectional illustration of an X-ray CT system according to an embodiment of the invention with a set of X-ray optical gratings that can be displaced in the direction of the system axis.
Figure 5:
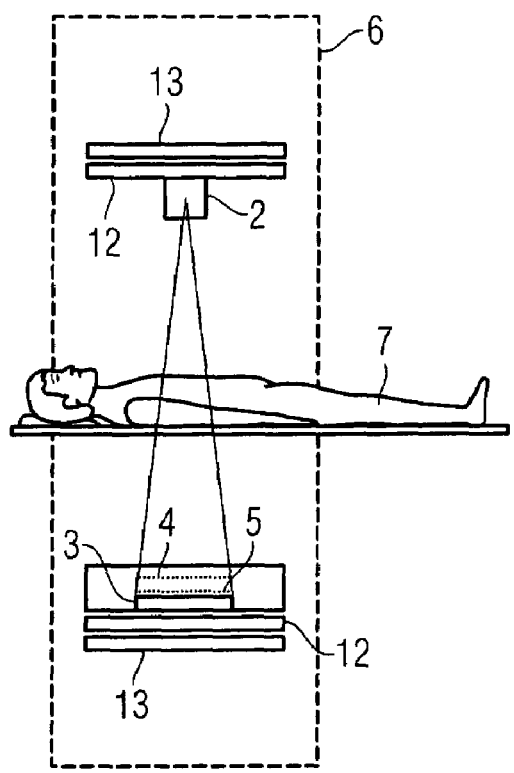
FIGS. 5-8 show longitudinal sections through different design variants of X-ray CT systems according to an embodiment of the invention.
Figure 6:
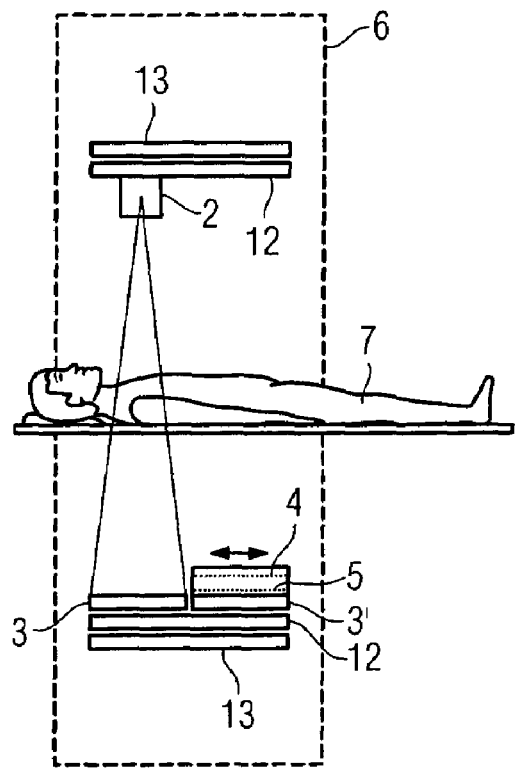

Another variant of an X-ray CT system according to an embodiment of the invention is illustrated in cross section in FIG. 4. This FIG. 4 corresponds substantially to the illustration from FIG. 2, but provided instead of the displacing apparatus of the type of a circular segment is a displacing apparatus in the direction of the system axis for the X-ray optical gratings 4 and 5 in the form of laterally arranged telescopic elements 17.1 and 17.2. The phase grating 4 and the analyzer grating 5 can be displaced in the direction of the system axis 9 with the aid of this telescopic displacing apparatus 17.1 and 17.2, such that it can optionally be pushed in between the patient 7 and the detector 3 for the purpose of measuring phase contrast.

Figure 7:
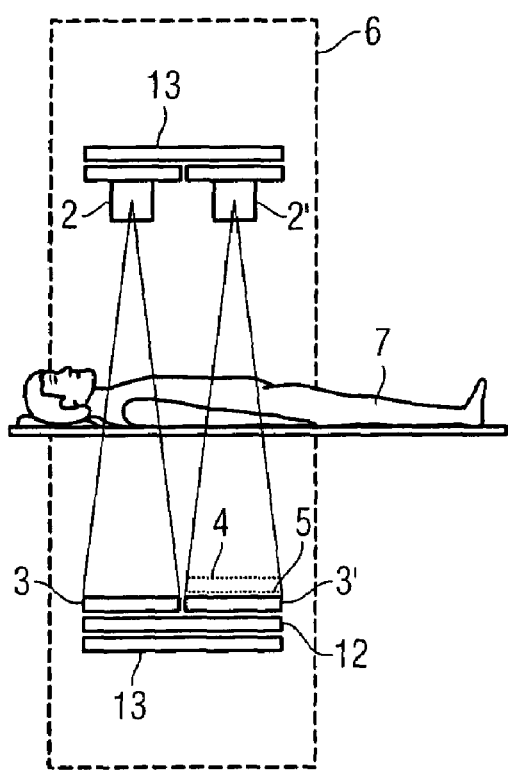
Figure 8:
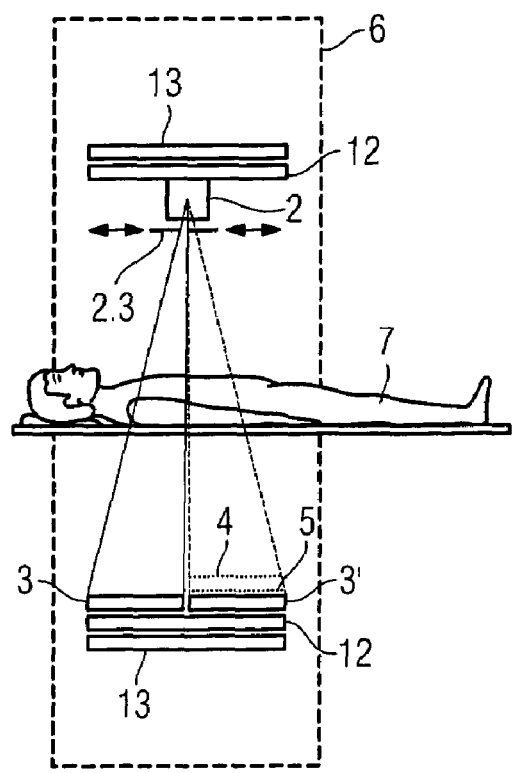

FIGS. 5 to 8 show variant refinements of the CT system according to an embodiment of the invention, in longitudinal section. Here, the variant from FIG. 5 corresponds to the refinement in accordance with FIG. 2, while FIG. 6 corresponds to the design of FIG. 4. FIG. 7 shows a design variant with focus/detector systems, which are arranged offset in the direction of the system axis and can be operated separately, having two X-ray tubes, the left-hand pairing with the X-ray tube 2 and the detector 3 being used for absorption measurement and the right-hand pairing with the X-ray tube 2', the detector 3' and the X-ray optical gratings 4 and 5 including the associated second rotor 12' being used for measuring phase contrast. FIG. 8 once again shows an alternative system to FIG. 7 use being made here of a single X-ray tube 2 that, however, has diaphragms 2.3 that can be moved in the direction of the system axis and permit the beam cone of the X-ray tube to be adapted as required depending on the use of the pure absorption detector 3 and/or the phase contrast detector 3'.

Thus, at least one embodiment of the invention presents an X-ray CT system that, on the one hand, permits phase contrast to be measured, and on the other hand the known absorption measurement is possible by using a low dose rate. It is also possible with this design to construct the CT system in a modular fashion such that a conservative absorption tomography system can be retrofitted later without a problem in order to form a phase contrast tomography system.

It goes without saying that the abovenamed features of the invention can be used not only in the combination respectively specified, but also in other combinations or on their own without departing from the scope of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray CT system for producing tomographic phase contrast and absorption images, comprising:
    a gantry, including a stationary stator and a first rotor supported on the stator to rotate relative to the stator about a system axis;
    at least one X-ray source detector system to rotate about a patient and a system axis and arranged on the first rotor; and
    at least one set of X-ray optical gratings for determining phase contrast, wherein the at least one set of X-ray optical gratings is arranged to be displaced relative to the first rotor of the gantry.

2. The X-ray CT system as claimed in claim 1, wherein the at least one set of X-ray optical gratings, in the operating state, covers only a part of the detector.

3. The X-ray CT system as claimed in claim 1, wherein, in addition to the rotor on which at least one X-ray source and at least one detector are fastened, the gantry Includes a displacing apparatus on which the X-ray optical gratings are arrangeable on the beam path, are fastened, and with the aid of which the gratings are displaceable from the beam path and into the beam path of the X-ray source.

4. The X-ray CT system as claimed in claim 3, wherein the displacing apparatus on which the X-ray optical gratings, arrangeable in the beam path, are fastened, is designed in the shape of a circular segment and fastened on the first rotor.

5. The X-ray CT system as claimed in claim 3, wherein the displacing apparatus on which the X-ray optical gratings, arrangeable in the beam path, are fastened, is designed as a second rotor.

6. The X-ray CT system as claimed in claim 1, wherein the X-ray optical gratings are fastened to be displaceable in the direction of the system axis.

7. The X-ray CT system as claimed in claim 1, wherein the X-ray optical gratings are designed to be displaceable in the direction of rotation relative to the first rotor.

8. The X-ray CT system as claimed in claim 2, wherein the X-ray source includes a diaphragm to adapt the emitted beam cone to the extent of at least one of the X-ray optical gratings and the overall detector.

9. The X-ray CT system as claimed in claim 1, wherein at least one X-ray source includes a source grating.

10. The X-ray CT system as claimed in claim 1, wherein a first beam path is provided exclusively for absorption measurement and a second beam path, arranged offset in the direction of the system axis, is provided for phase contrast measurement.

11. The X-ray CT system as claimed in claim 10, wherein the gantry includes a second rotor, one detector being arranged on the first rotor for absorption measurement, and a second detector being arranged on the second rotor exclusively for phase contrast measurement with the aid of the set of X-ray optical gratings.

12. The X-ray CT system as claimed in claim 10, wherein a dedicated X-ray source is arranged on each rotor.

13. The X-ray CT system as claimed in claim 2, wherein the X-ray optical gratings are fastened to be displaceable in the direction of the system axis.

14. The X-ray CT system as claimed in claim 2, wherein the X-ray optical gratings are designed to be displaceable in the direction of rotation relative to the first rotor.

15. The X-ray CT system as claimed in claim 3, wherein the X-ray optical gratings are fastened to be displaceable in the direction of the system axis.

16. The X-ray CT system as claimed in claim 3, wherein the X-ray optical gratings are designed to be displaceable in the direction of rotation relative to the first rotor.

17. The X-ray CT system as claimed in claim 3, wherein the X-ray source includes a diaphragm to adapt the emitted beam cone to the extent of at least one of the X-ray optical gratings and the overall detector.

18. The X-ray CT system as claimed in claim 2, wherein at least one X-ray source includes a source grating.

19. The X-ray CT system as claimed in claim 3, wherein at least one X-ray source includes a source grating.

20. The X-ray CT system as claimed in claim 11, wherein a dedicated X-ray source is arranged on each rotor.

* * * * *